United States Patent [19]

Maruyama et al.

[11] 4,009,275
[45] Feb. 22, 1977

[54] PHENOXYPROPYLAMINE DERIVATIVES

[75] Inventors: Isamu Maruyama, Minoo; Masaru Nakao; Kikuo Sasajima, both of Toyonaka, Japan; Shigeho Inaba, Takarazuka; Hisao Yamamoto, Kobe, all of Japan

[73] Assignee: Sumitomo Chemical Company, Limited, Japan

[22] Filed: Feb. 28, 1975

[21] Appl. No.: 553,932

[30] Foreign Application Priority Data

Feb. 28, 1974 Japan .................... 49-24501
May 9, 1974 Japan .................... 49-51921
Oct. 9, 1974 Japan .................... 49-116614

[52] U.S. Cl. .................... 424/267; 260/293.6
[51] Int. Cl.² .................... C07D 401/04
[58] Field of Search .................... 260/293.6; 424/267

[56] References Cited

UNITED STATES PATENTS

| | | | |
|---|---|---|---|
| 3,161,645 | 12/1964 | Janssen | 260/293.6 |
| 3,225,052 | 12/1965 | Janssen | 260/293.6 |
| 3,840,529 | 10/1974 | Maruyama et al. | 260/293.6 |

*Primary Examiner*—Natalie Trousof
*Assistant Examiner*—C. M. S. Jaisle
*Attorney, Agent, or Firm*—Stewart and Kolasch, Ltd.

[57] ABSTRACT

Phenoxypropylamine derivatives of the formula:

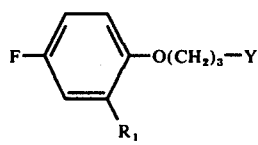

wherein Y is

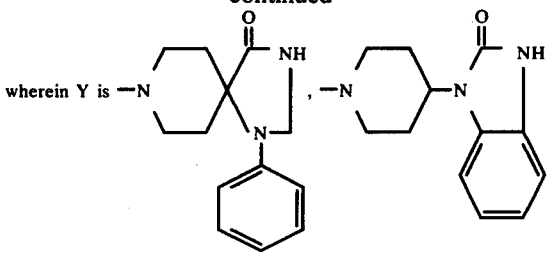

or

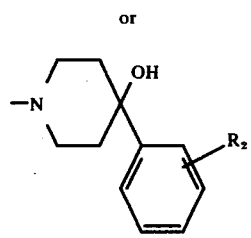

(in which $R_2$ is a halogen atom or a trifluoromethyl group) and $R_1$ is a halogen atom or a $C_1$–$C_4$ alkyl or $C_2$–$C_4$ alkenyl group, and their pharmaceutically acceptable salts, which are useful as neuroleptic agents and can be prepared by reacting a compound of the formula:

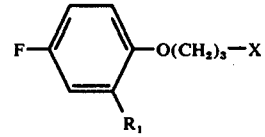

wherein X is a halogen atom and $R_1$ is as defined above with a compound of the formula:

H–Y wherein Y is as defined above.

3 Claims, No Drawings

PHENOXYPROPYLAMINE DERIVATIVES

The present invention relates to novel phenoxypropylamine derivatives, and their preparation and use.

The objective phenoxypropylamine derivatives are represented by the formula:

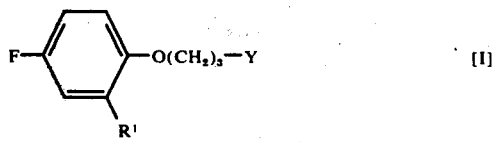

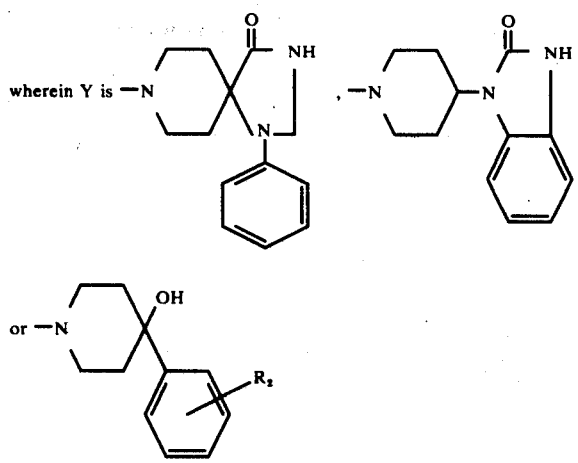

(in which $R_2$ is a halogen atom or a trifluoromethyl group) and $R_1$ is a halogen atom or a $C_1$-$C_4$ alkyl or $C_2$-$C_4$ alkenyl group.

The phenoxypropylamine derivatives [I] can form pharmaceutically acceptable salts with a variety of inorganic and organic acids such as sulfuric, phosphoric, hydrochloric, hydrobromic, nitric, oxalic, malonic, succinic, lactic, tartaric, maleic, fumaric, formic, acetic, salicylic and p-toluenesulfonic acids.

So far, in U.S. Pat. No. 3,225,052, there are disclosed some phenoxypropylamine type compounds having a basic structure similar to that of the phenoxypropylamine derivatives [I]. Their neuroleptic activity is, however, not satisfactory.

As the result of the study seeking new compounds having a more potent neuroleptic activity, it has been found that, among the phenoxypropylamine type compounds, the phenoxypropylamine derivatives [I] of the present invention characteristically have an excellent neuroleptic activity.

The structural characteristic of the phenoxypropylamine derivatives [I] is the presence of the substituent represented by the symbol $R_1$ in addition to the fluorine atom on the benzene ring of the phenoxy group. The particularly preferable class of the phenoxypropylamine derivatives [I] is the compounds of the formula:

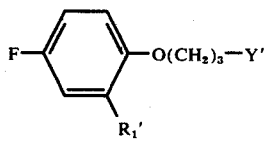

a chlorine atom or an allyl group, and their pharmaceutically acceptable salts.

The phenoxypropylamine derivatives [I] and their pharmaceutically acceptable salts can be administered orally in conventional dosage forms such as a tablet, capsule, solution, suspension, elixir and the like.

A typical tablet may be constituted by from 1 to 20 percent by weight of a binder (e.g. tragacanth), from 1 to 20 percent by weight of a lubricant (e.g. talcum, magnesium stearate), an average dose of the active ingredient and q.s. 100 percent by weight of a filler (e.g. lactose). The usual oral dosage of the active ingredient may be from 1 to 1000 mg per day.

Accordingly, a basic object of the present invention is to provide novel phenoxypropylamine derivatives [I] and their pharmaceutically acceptable salts, which have excellent pharmacological properties. Another object of this invention is to provide processes for producing such novel and useful phenoxypropylamine derivatives [I] and their salts. A further object of the invention is to provide pharmaceutical compositions comprising at least one of such novel and useful phenoxypropylamine derivatives [I] and their salts. These and other objects of the invention will be apparent from the foregoing and subsequent descriptions.

According to the present invention, the novel phenoxypropylamine derivative [I] can be prepared by reacting a compound of the formula:

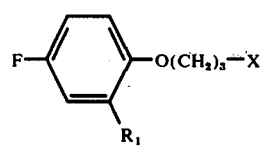

wherein X is a halogen atom and $R_1$ is as defined above, with a compound of the formula:

H–Y [III]

wherein Y is as defined above, or by reacting a compound of the formula:

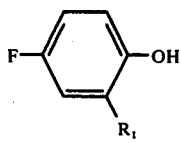

[IV]

wherein $R_1$ is as defined above, with a compound of the formula:

$$X-(CH_2)_3-Y \quad [V]$$

wherein X and Y are each as defined above.

The reaction may be carried out in the absence or presence of an acid acceptor in an inert organic solvent (e.g. benzene, toluene, xylene, dimethylformamide, pyridine, methanol, ethanol) at a temperature from about room temperature to the boiling temperature of the solvent used. Suitable acid acceptors include sodium carbonate, potassium carbonate, sodium bicarbonate, potassium bicarbonate, sodium hydroxide, potassium hydroxide, sodium hydride, potassium hydride, triethylamine, etc.

The phenoxypropylamine derivative [I] can also be prepared by reducing a compound of the formula:

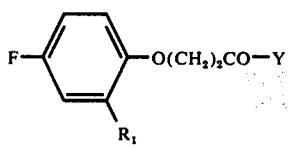

[VI]

wherein Y and $R_1$ are each as defined above, with a reducing agent.

Preferred examples of the reducing agent are metal hydride complexes such as lithium aluminum hydride, lithium aluminum hydride-aluminum chloride, sodium borohydride-aluminum chloride and sodium borohydride-boron trifluoride. The reaction is usually effected in the presence of a solvent (e.g. water, ethanol, ether, tetrahydrofuran, dioxane, N-ethylmorpholine) at a wide range of temperature, for instance, while cooling, at room temperature or under an elevated temperature.

The said compounds [II], [V] and [VI] may be produced by conventional procedures, for instance, as shown in the following reaction scheme:

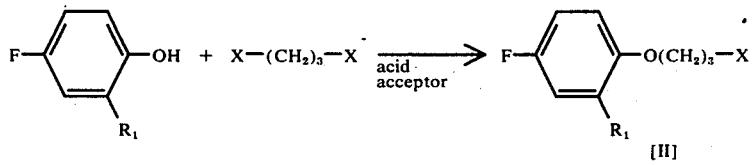

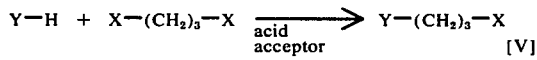

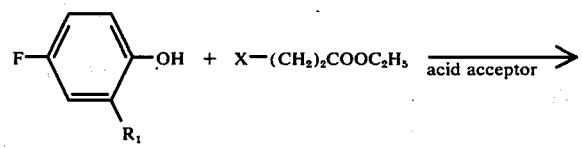

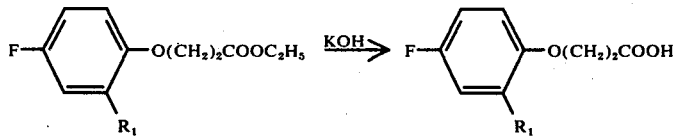

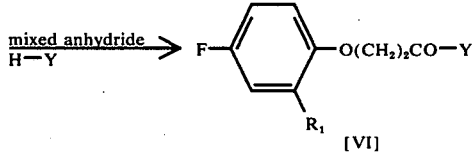

wherein $R_1$, X and Y are each as defined above.

When the thus obtained phenoxypropylamine derivative [I] is in a free base form, it may be converted into the acid-addition salt by interaction with an acid. In like manner, the free base can be regenerated from the acid-addition salt in a conventional procedure, for instance, by treating with a strong base (e.g., alkali metal hydroxide, alkali metal carbonate, alkali metal bicarbonate). The base thus regenerated can then be interacted with an acid to give the corresponding acid-addition salt.

The present invention is further disclosed in the following examples of more preferred embodiments thereof, which are presented for the purpose of illustration, and it is not intended to limit the scope of the invention, thereby.

EXAMPLE 1

A mixture of 3.3 g of 2-(3-chloropropoxy)-5-fluorochlorobenzene, 3.3 g of 1-(4-piperidinyl)-2-oxobenzimidazoline, 0.9 g of sodium carbonate and 80 ml of dimethylformamide was heated at 80° – 90° C for 15 hours. After cooling, the reaction mixture was poured into water and extracted with benzene. The extract was washed with water, dried over anhydrous sodium sulfate and evaporated under reduced pressure. The residue was triturated with ether, cooled and filtered to give 1-{3-(2-chloro-4-fluorophenoxy)propyl}-4-(2-oxo-1-benzimidazolinyl)piperidine, m.p. 130° – 132° C; recrystallized from benzenecyclohexane, m.p. 149° – 149.5° C.

The following compounds were obtained in the same manner as above:

8-{3-(2-Chloro-4-fluorophenoxy)propyl}-1-phenyl-4-oxo-1,3,8-triazaspiro[4,5]decane, m.p. 155° – 156° C;

1-{3-(2-Chloro-4-fluorophenoxy)propyl}-4-(4-chlorophenyl)-4-hydroxypiperidine, m.p. 130° – 131° C;

1-{3-(2-Allyl-4-fluorophenoxy)propyl}-4-(2-oxo-1-benzimidazolinyl)piperidine hydrochloride, m.p. 192° – 192.5° C (decomp.);

8-{3-(2-Allyl-4-fluorophenoxy)propyl}-1-phenyl-4-oxo-1,3,8-triazaspiro [4,5]decane, m.p. 117° – 117.5° C;

1-{3-(2-Allyl-4-fluorophenoxy)propyl}-4-(4-chlorophenyl)-4-hydroxypiperidine, m.p. 118° – 119° C;

1-{3-(2-Allyl-4-fluorophenoxy)propyl}-4-hydroxy-4-(3-trifluoromethylphenyl)piperidine hydrochloride, m.p. 130° – 130.5° C (decomp.);

1-{3-(4-Fluoro-2-n-propylphenoxy)propyl}-4-(2-oxo-1-benzimidazolinyl)piperidine, m.p. 100° – 101° C;

8-{3-(4-Fluoro-2-n-propylphenoxy)propyl}-1-phenyl-4-oxo-1,3,8-triazaspiro[4,5]decane, m.p. 93° – 94° C;

4-(4-Chlorophenyl)-4-hydroxy-1-{3-(4-fluoro-2-n-propylphenoxy)propyl}piperidine, m.p. 100° – 101° C;

1-{3-(4-Fluoro-2-n-propylphenoxy)propyl}-4-hydroxy-4-(3-trifluoromethylphenyl)piperidine hydrochloride, m.p. 122° – 123° C.

EXAMPLE 2

A mixture of 1.5 g of 2-allyl-4-fluorophenol, 3.1 g of 8-(3-chloropropyl)-1-phenyl-4-oxo-1,3,8-triazaspiro[4,5]decane, 0.7 g of potassium carbonate and 40 ml of toluene was heated under reflux for 10 hours. After cooling, the reaction mixture was washed with water, dried over sodium sulfate and evaporated under reduced pressure. The residue was triturated with ether, cooled and filtered to give 8-{3-(2-allyl-4-fluorophenoxy)propyl}-1-phenyl-4-oxo-1,3,8-triazaspiro[4,5]decane, m.p. 110° – 113° C; recrystallized from cyclohexane, m.p. 117° – 117.5° C.

EXAMPLE 3

A mixture of 0.4 g of lithium aluminum hydride, 2.2 g of 8-{3-(2-chloro-4-fluorophenoxy)propionyl}-1-phenyl-4-oxo-1,3,8-triazaspiro[4,5]decane and 40 ml of tetrahydrofuran was heated under reflux for 3 hours. To the reaction mixture were added gradually water and chloroform under cooling, and the precipitate was filtered off. The organic layer was separated, dried over sodium sulfate and evaporated under reduced pressure. The residue was triturated with ether, cooled and filtered to give 8-{3-(2-chloro-4-fluorophenoxy)propyl}-1-phenyl-4-oxo-1,3,8-triazaspiro-[4,5]decane, m.p. 154° – 155° C; recrystallized from benzenecyclohexane, m.p. 155° – 156° C.

What is claimed is:

1. A phenoxypropylamine derivative of the formula:

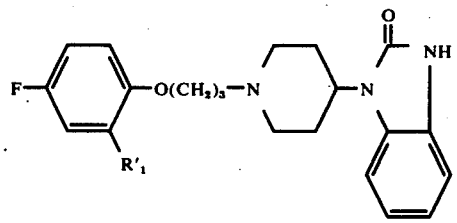

wherein $R_1'$ is a chlorine atom or an allyl group, and pharmaceutically acceptable salts thereof.

2. A pharmaceutical composition comprising from 1 to 1000 mg. of the phenoxypropylamine derivative of claim 1 as an active ingredient and a pharmaceutically acceptable carrier or diluent.

3. A method for using the phenoxypropylamine derivative of claim 1 as a neuroleptic agent which comprises orally administering to a subject from 1 to 1000 mg. per day of said derivative.

* * * * *